United States Patent
Falahee

(10) Patent No.: US 8,882,841 B2
(45) Date of Patent: Nov. 11, 2014

(54) STEERABLE INTERBODY FUSION CAGE

(75) Inventor: Mark H. Falahee, Ann Arbor, MI (US)

(73) Assignee: US Spine, Inc., Salt Lake City, UT (US)

( * ) Notice: Subject to any disclaimer, the term of this patent is extended or adjusted under 35 U.S.C. 154(b) by 1996 days.

(21) Appl. No.: 11/532,731

(22) Filed: Sep. 18, 2006

(65) Prior Publication Data

US 2007/0067035 A1    Mar. 22, 2007

Related U.S. Application Data

(60) Provisional application No. 61/718,063, filed on Sep. 16, 2005.

(51) Int. Cl.
- *A61F 2/44* (2006.01)
- *A61F 2/46* (2006.01)
- *A61F 2/30* (2006.01)
- *A61F 2/28* (2006.01)

(52) U.S. Cl.
CPC ....... *A61F 2/4455* (2013.01); *A61F 2230/0004* (2013.01); *A61F 2002/4415* (2013.01); *A61F 2002/4629* (2013.01); *A61F 2220/0091* (2013.01); *A61F 2230/0015* (2013.01); *A61F 2002/3082* (2013.01); *A61F 2002/30565* (2013.01); *A61F 2210/0014* (2013.01); *A61F 2002/2835* (2013.01); *A61F 2002/30133* (2013.01); *A61F 2002/30471* (2013.01); *A61F 2002/30092* (2013.01); *A61F 2002/30112* (2013.01)
USPC ..................................................... 623/17.16

(58) Field of Classification Search
USPC ............................ 623/17.11–17.16
See application file for complete search history.

(56) References Cited

U.S. PATENT DOCUMENTS

| | | | |
|---|---|---|---|
| 4,501,269 A | 2/1985 | Bagby | |
| 6,039,761 A * | 3/2000 | Li et al. | 623/17.16 |
| 6,126,689 A * | 10/2000 | Brett | 623/17.16 |
| 6,387,130 B1 * | 5/2002 | Stone et al. | 623/17.16 |
| 6,409,766 B1 * | 6/2002 | Brett | 623/17.16 |
| 6,599,294 B2 * | 7/2003 | Fuss et al. | 606/99 |
| 6,805,697 B1 | 10/2004 | Helm et al. | |
| 6,830,570 B1 | 12/2004 | Frey et al. | |
| 7,018,413 B2 * | 3/2006 | Kruger | 623/17.11 |
| 7,306,628 B2 * | 12/2007 | Zucherman et al. | 623/17.11 |
| 7,361,193 B2 * | 4/2008 | Frey et al. | 623/17.16 |
| 2005/0038514 A1 | 2/2005 | Helm et al. | |
| 2005/0096745 A1 * | 5/2005 | Andre et al. | 623/17.11 |
| 2005/0119747 A1 * | 6/2005 | Fabris Monterumici et al. | 623/17.11 |
| 2005/0283245 A1 * | 12/2005 | Gordon et al. | 623/17.15 |
| 2006/0142858 A1 * | 6/2006 | Colleran et al. | 623/17.11 |
| 2006/0265065 A1 * | 11/2006 | Bagga et al. | 623/17.11 |
| 2007/0225810 A1 * | 9/2007 | Colleran et al. | 623/17.13 |
| 2007/0260314 A1 * | 11/2007 | Biyani | 623/17.11 |

* cited by examiner

*Primary Examiner* — Matthew Lawson
(74) *Attorney, Agent, or Firm* — Phillips Ryther & Winchester; Matthew D. Thayne

(57) ABSTRACT

An interbody vertebral cage facilitates minimally invasive approaches to the intervertebral disc for corrective restoration of disc height, stabilization between vertebra, and fusion. The preferred embodiment provides a streamlined, slender straight contour with a central hinge or other articulating apparatus that allows the introduction of the cage into the operative field and disc space in a minimally invasive, bone-sparing manner. After partial insertion, the hinge component is activated, allowing the operator to steer the cage anterior-medially within the disc space to an anterior-central position within the intervertebral space. In this state the cage is shaped like a crescent, chevron or boomerang.

20 Claims, 2 Drawing Sheets

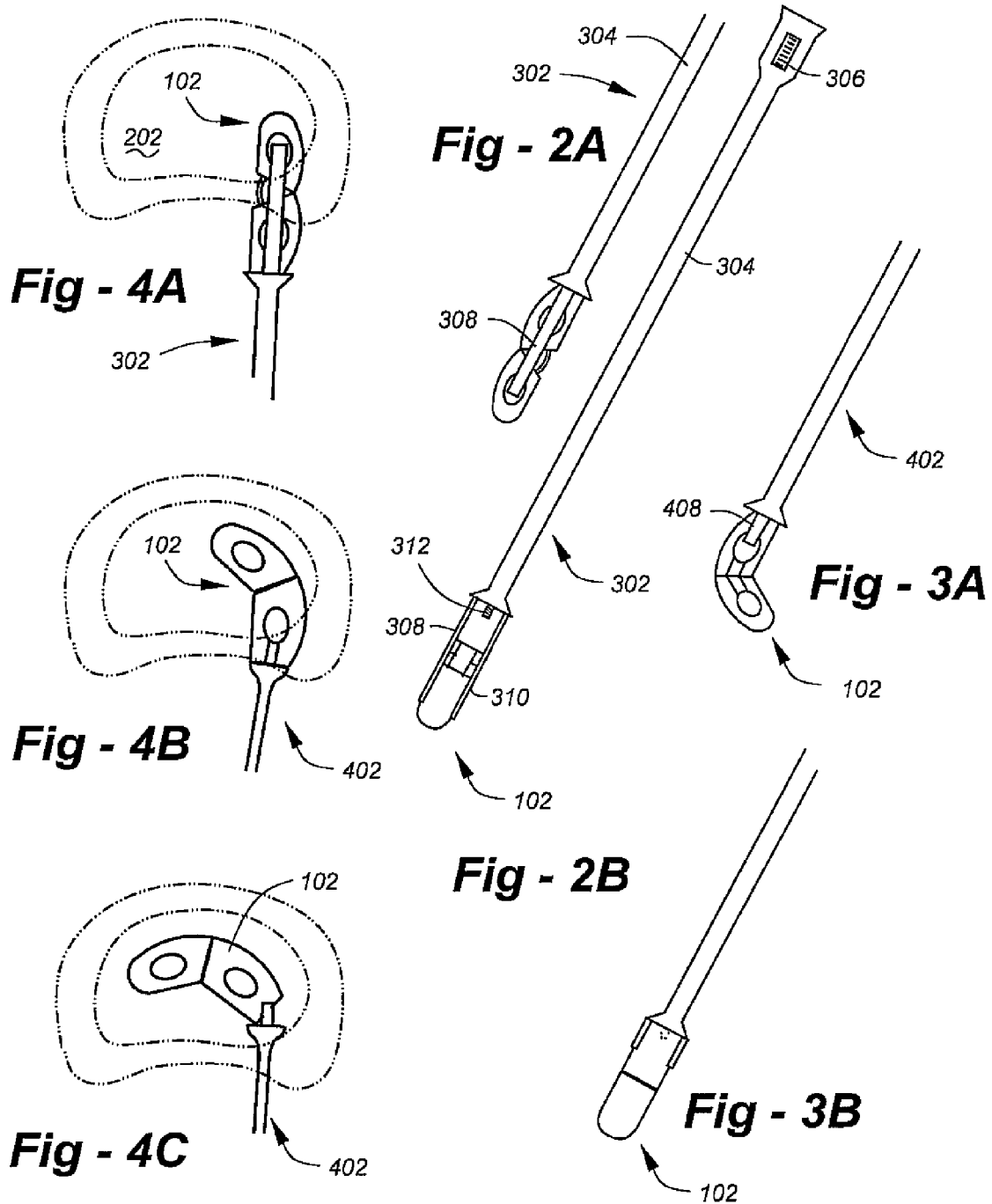

STEERABLE INTERBODY FUSION CAGE

REFERENCE TO RELATED APPLICATION

This application claims priority from U.S. Provisional Patent Application Ser. No. 60/718,063, filed Sep. 16, 2005, the entire content of which is incorporated herein by reference.

FIELD OF THE INVENTION

This invention relates generally to intervertebral cages and, in particular, to a steerable interbody fusion cage applicable to minimally invasive surgical (MIS) procedures.

BACKGROUND OF THE INVENTION

One of the most common causes of chronic back pain is degenerative disc disease. The degeneration may start after a particular injury, or many occur due to multiple injuries over time. Degeneration usually takes several years. As the vertebrae grow closer, the openings in the back of the spine where the nerve roots leave the spinal canal become narrower. This can lead to pinching and irritation on the nerves, causing pain.

There are many surgical approaches and methods used to fuse the spine. Most involve the placement of a bone graft between the vertebrae. Supplemental hardware, such as plates, screws and cages may or may not be used, depending upon the indication.

An early cage design is described in U.S. Pat. No. 4,501,269 to Bagby, entitled "PROCESS FOR FUSING BONE JOINTS." According to the method, a hole is bored transversely across the joint and a slightly larger cylindrical basket is driven into the hole, thereby spreading the bones in resistance to the tensile forces of the surrounding tissue. Immediate stabilization of the joint is achieved by the implantation of the rigid cylindrical basket. Subsequent bone-to-bone fusion is achieved, both through and about the basket, which is filled with bone fragments produced during the boring step.

The Bagby patent states that the process is applicable to any human or animal joint formed by opposed contiguous bony surfaces which are covered and separated by intervening cartilage and are surrounded by ligaments which resist expansion of the joint. Specific examples of such joints are a spinal joint between adjacent vertebrae or the ankle joint.

This stand-alone interbody fusion technique continued to evolve with material changes and the design of threaded cages to increase stability and decrease displacement rates. Bilateral, parallel implants were designed for use in the lumbar spine, with the first human implantation occurring in the early 1990s. The cylindrical titanium cages were threaded to screw into the endplates, thereby stabilizing the device and allowing for increased fusion rate with a stand-alone anterior device.

Ray and colleagues developed a similar titanium interbody fusion device which was initially used in posterior lumbar interbody fusions (PLIF), but expanded to include ALIF procedures (anterior lumbar interbody fusions). In 1985, Otero-Vich reported using threaded bone dowels for anterior cervical arthrodesis, and femoral ring allograft bone has subsequently been fashioned into cylindrical threaded dowels for lumbar application.

Currently, there are a wide number of available interbody fusion devices of varying design and material, including:
1) Cylindrical threaded titanium interbody cages;
2) Cylindrical threaded cortical bone dowels; and
3) Vertical interbody rings, boxes and wedges.

A typical intervertebral fusion cage is a large, hollow cylinder made of some type of metal, usually titanium. It is designed as a "cage" so that bone graft can be placed inside the hollow cylinder. Holes throughout the cage allow bone to form around and through the cage to allow a spinal fusion to occur between two vertebrae. Many of the newer types of intervertebral fusion cages are also designed to facilitate an open incision or a laparoscopic procedure.

An intervertebral fusion cage serves a couple important purposes. First, it distracts the vertebrae, making more room for the nerves, thereby decreasing pinching and irritation. The strong ligaments that surround the disc are also tightened, which decreases the segmental instability between the two vertebrae and decreases the mechanical pain in the spine. The cage also holds the two vertebrae in the correct position until a fusion occurs.

There are several drawbacks with existing approaches and techniques, such that further research and improved designs are desirable. Increased morbidity of anterior in-situ cage placement is not justified when less anatomic correction of the disc space is possible. Additionally, current PLIF and transverse lumbar interbody fusions (TLIF) cage and allograft placements require large dissections for exposure. PLIF and TLIF approaches also weaken existing posterior elements via bony destruction resulting from the operative procedure used to access the disc space.

SUMMARY OF THE INVENTION

This invention relates to interbody cages designed to facilitate minimally invasive approaches to the intervertebral disc for corrective restoration of disc height, stabilization between vertebra, and fusion. Cages according to the invention allow for a direct, minimally invasive, Posterior Lumbar Interbody Approach (PLIF) with preservation of the pars interarticularis and inferior facet of the superior vertebra. These bone elements are frequently sacrificed in the typical PLIF and TLIF approaches now in use with conventional designed cages.

The preferred embodiment provides a streamlined, slender straight contour with a central hinge or other articulating apparatus that allows the introduction of the cage into the operative field and disc space in a minimally invasive, bone-sparing manner. After partial insertion, the hinge component is activated, allowing the operator to steer the cage anterior-medially within the disc space to an anterior-central position within the intervertebral space. In this state the cage is shaped like a crescent, chevron or boomerang.

BRIEF DESCRIPTION OF THE DRAWINGS

FIG. 2A is a top-down view showing a long-armed introducer for insertion of the cage in a straightened condition;

FIG. 2B is a side-view drawing of the long-armed introducer;

FIG. 3A is a top-down view showing a short-armed introducer for steering the cage through a curved path;

FIG. 3B is a side-view drawing of the short-armed introducer;

FIG. 4A is a drawing showing an initial stage of cage insertion using the long-armed introducer instrument;

FIG. 4B is a drawing showing an intermediate stage of cage insertion through a curved path; and FIG. 4C is a drawing showing a final stage of cage insertion oriented in this case to anterior center of an intervertebral disc space.

DETAILED DESCRIPTION OF THE INVENTION

Figure 1A:
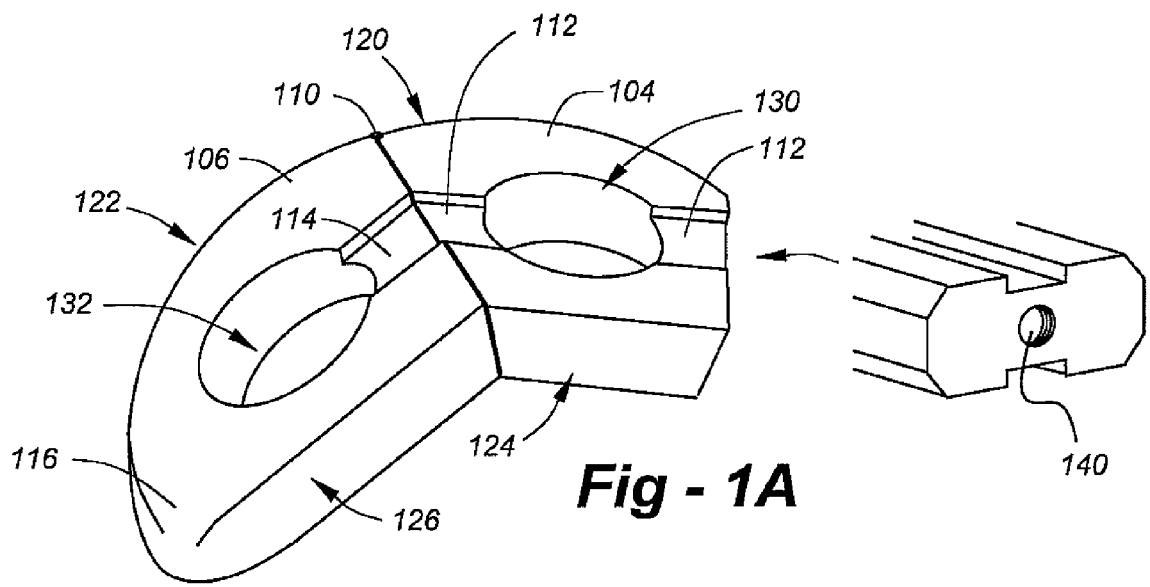
FIG. 1A is an oblique view of the preferred embodiment of the invention in a folded condition.

Making reference to the drawings, FIG. 1A is an oblique view of the preferred embodiment of the invention in a folded condition depicted generally at 102. The implant comprises a proximal portion 104 and a distal portion 106 joined by a hinge 110. Both portions include voids 130, 132 facilitating the introduction of bone graft and other biologic and or therapeutic substances. The proximal portion 104 includes a longitudinal recess 112, and the distal portion 106 includes a longitudinal recess 114. As shown in the end-view drawing at the right of FIG. 1A, these recesses are provided on the upper and lower surfaces of each portion. The end-view drawing also shows a central threaded hole 140 used for initial introduction.

In the preferred embodiment, the 'outer' surfaces 120, 122 of the respective portions 104, 106 are curved such that in the folded state of FIG. 1A a continuous outer surface is established. Although this is not necessary to the invention, curved surfaces better facilitate travel along a curved as discussed in further detail below. The 'inner' surfaces 124, 126 are preferably straight but may be curved as well. The distal portion preferably terminates in a smooth, blunt termination 116.

Figure 1B:
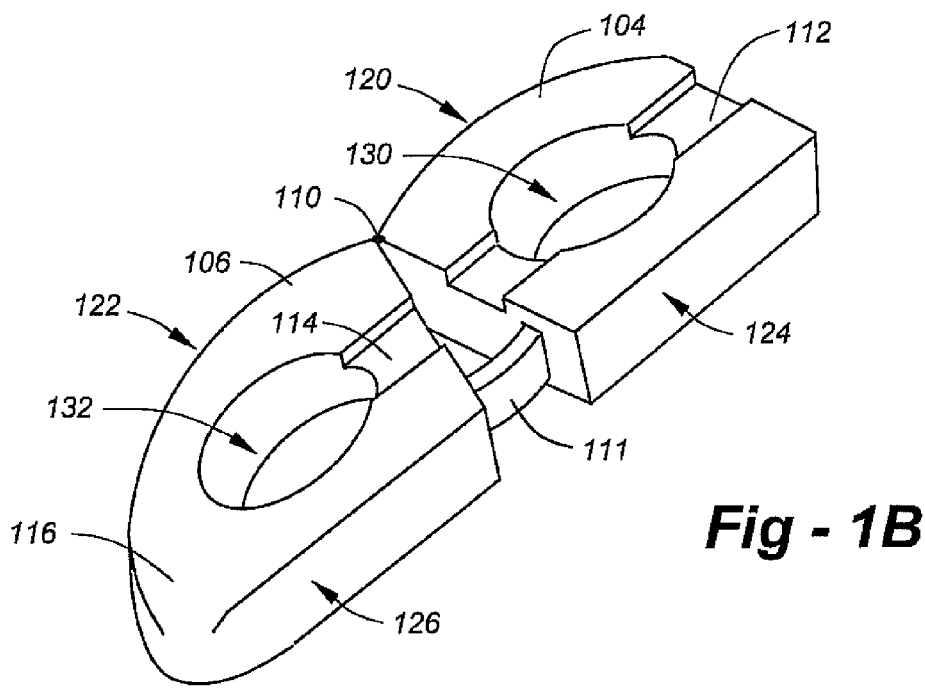
FIG. 1B is an oblique view of the preferred embodiment of the invention in an unfolded or straightened condition.

In the folded condition of FIG. 1A, recesses 112 and 114 on proximal and distal portions are not aligned, but rather form an angle. In the preferred embodiment in the folded condition the axes of the proximal and distal portions form an angle on the order of 40 degrees to optimize anterior medial positioning as described herein below. However, in the straightened condition of FIG. 1B, the recesses are aligned. FIG. 1B also shows the optional addition of a member 111 that stabilizes the hinging action while ensuring that the proximal and medial portions do not over-articulate.

FIG. 2A is a top-down view showing a long-armed introducer 302 used for inserting the cage in the straightened condition of FIG. 1B. The instrument includes a shaft 304 and a long arm 308 that fits into the recesses 112 and 114 of the proximal and distal portions, respectively. A bottom long arm 310 configured to fit into the bottom recesses of the proximal and portions as shown in FIG. 1A. At the proximal end of the long-armed introducer 302 is a thumbwheel to turn screw 312 to engage and disengage threads 140 shown in FIG. 1A. FIG. 2B is a side-view drawing of the long-armed introducer.

FIG. 3A is a top-down view showing a short-armed introducer 402 for steering the cage 102 through a curved path, and FIG. 3B is a side-view drawing of the short-armed introducer. This instrument has short arms such as 408 which engage only with the proximal portion of the cage, thereby facilitating articulation.

FIG. 4A is a drawing showing an initial stage of cage insertion using the long-armed introducer instrument 302. At this stage the cage 102 has just entered intradiscal space 202. FIG. 4B is a drawing showing an intermediate stage of cage insertion. Note that the long-armed introducer instrument 302 has been replaced with the short-armed introducer instrument 402, allowing travel through a curved path. FIG. 4C is a drawing showing a final stage of cage insertion oriented in this case to anterior center of an intervertebral disc space.

As an alternative the final position shown in FIG. 4C, the cage may be left in the straight or open position for one-sided fixation. In the preferred embodiment, the cage is mirror-image symmetrical such that it may be flipped over and used for introduction into the other side of the body, regardless of whether straight or curved trajectory is deployed. The slender profile of the cage allows for bone and or osteoinductive/conductive materials to be placed within its walls, with additional room posterior to the cage for further grafting. The cage can be constructed of any biologically compatible material, including PEEK, PEK, carbon fiber, or other materials, radiolucent or otherwise.

In the preferred embodiment, the shape of cage anteriorly is contoured much like a rounded or bullet shape to facilitate anterior-central penetration. The posterior "docking portion" of the cage is flat to accommodate the introduction and driving tools and provides a stable surface for impact. Removal of the cage may be done via reversal of the insertion steps. Although only a single "hinge" is depicted, multiple points of articulation may be used, much like train cars that turn a corner. In addition, although the cage may bend and steer on its own, more active mechanisms such as springs and/or shape-memory materials may be used.

I claim:

1. A method of fusing vertebrae, comprising the steps of:
providing a steerable intervertebral cage comprising:
a distal portion having front, back, top, bottom, inner and outer surfaces;
a proximal portion having a front, back, top, bottom, inner and outer surfaces, and
a hinge joining the front of the proximal portion to the back of the distal portion, such that the cage has a first, straightened shape with the hinge open and a second, crescent shape with the hinge closed;
introducing the cage in the first, straightened shape into an anterior central position within an intervertebral disc space using a posterior lumbar interbody fusion (PLIF) or transverse lumbar interbody fusion (TLIF) approach;
steering or allowing the cage to assume the second, crescent shape once within the intervertebral disc space; and
wherein the method further includes the steps of:
using a first instrument to maintain the cage in the straightened shape for introduction; and
switching to a different instrument that facilitates articulation and final positioning.

2. The method of claim 1, wherein the first instrument comprises a long-armed introducer, and wherein the different instrument comprises a second instrument comprising a short-armed introducer.

3. The method of claim 2, wherein the long-armed introducer comprises a long arm configured to engage the steerable intervertebral cage, wherein the short-armed introducer comprises a short arm configured to engage the steerable intervertebral cage, and wherein the short arm has a length less than the long arm.

4. The method of claim 3, wherein the long-armed introducer comprises a pair of arms configured to engage the steerable intervertebral cage on opposite sides of the steerable intervertebral cage.

5. The method of claim 4, wherein the short-armed introducer comprises a pair of arms configured to engage the steerable intervertebral cage on opposite sides of the steerable intervertebral cage.

6. The method of claim 2, wherein the long-armed introducer is configured to engage the steerable intervertebral cage along a greater portion of the steerable intervertebral cage than the short-armed introducer.

7. The method of claim 1, further comprising engaging the first instrument with a first longitudinal recess formed on the proximal portion of the steerable intervertebral cage and engaging the first instrument with a second longitudinal recess formed on the distal portion of the steerable intervertebral cage.

8. The method of claim 7, further comprising engaging the different instrument with the first longitudinal recess formed on the proximal portion of the steerable intervertebral cage.

9. The method of claim 8, further comprising closing the hinge such that the first longitudinal recess is aligned with the second longitudinal recess.

10. The method of claim 9, further comprising steering the steerable intervertebral cage through a curved path using the different instrument.

11. The method of claim 10, wherein the steerable intervertebral cage further comprises a stabilizing member configured to stabilize a hinging action of the hinge of the steerable intervertebral cage.

12. The method of claim 11, wherein the stabilizing member is positioned so as to couple the proximal portion of the steerable intervertebral cage with the distal portion of the steerable intervertebral cage.

13. The method of claim 1, wherein the steerable intervertebral cage comprises a symmetrical cage configured such that the symmetrical cage can be introduced into opposite sides of a patient's body by flipping the symmetrical cage over.

14. The method of claim 1, wherein the steerable intervertebral cage further comprises an anterior portion comprising a curved surface configured to facilitate penetration into the intervertebral disc space, and wherein the step of introducing the cage comprises introducing the cage into an anterior-central position within the intervertebral disc space with the anterior portion entering the intervertebral disc space first.

15. The method of claim 14, wherein the steerable intervertebral cage further comprises a posterior portion configured to engage with at least one of the first instrument and the different instrument.

16. The method of claim 15, wherein the posterior portion comprises a flat surface.

17. The method of claim 16, wherein the posterior portion comprises a threaded opening positioned within the flat surface.

18. The method of claim 1, wherein the proximal portion of the steerable intervertebral cage forms an angle with respect to the distal portion of the steerable intervertebral cage on the order of 40 degrees when the steerable intervertebral cage is in the straightened shape.

19. The method of claim 1, wherein the outer surface of the distal portion of the steerable intervertebral cage comprises a curved surface, and wherein the outer surface of the proximal portion of the steerable intervertebral cage comprises a curved surface.

20. The method of claim 19, wherein the steerable intervertebral cage is configured such that the curved surface of the distal portion and the curved surface of the proximal portion form a continuous outer curved surface in the crescent shape.

* * * * *